United States Patent [19]

Elmaleh et al.

[11] Patent Number: 5,587,398
[45] Date of Patent: Dec. 24, 1996

[54] META SUBSTITUTED ARYLALKYLAMINES AND THERAPEUTIC AND DIAGNOSTIC USES THEREFOR

[75] Inventors: David R. Elmaleh, 38 Hartman Rd., Newton, Mass. 02159; Alan J. Fischman, Boston, Mass.

[73] Assignee: David R. Elmaleh, Newton, Mass.

[21] Appl. No.: 461,577

[22] Filed: Jun. 2, 1995

Related U.S. Application Data

[63] Continuation-in-part of Ser. No. 265,512, Jun. 24, 1994, abandoned, which is a continuation-in-part of Ser. No. 254,032, Jun. 3, 1994, abandoned.

[51] Int. Cl.$^6$ .......................... A61K 31/135; C07C 15/04
[52] U.S. Cl. .......................... 514/654; 514/646; 514/909; 564/305; 564/336; 564/374; 564/381; 564/382
[58] Field of Search .................................. 514/654, 646, 514/909; 564/305, 336, 374, 381, 382

[56] References Cited

U.S. PATENT DOCUMENTS

| | | | |
|---|---|---|---|
| 3,663,595 | 5/1972 | Beregi et al. | 260/471 |
| 3,733,339 | 5/1973 | Horrom | 260/340.5 |
| 3,769,319 | 10/1973 | Boitze et al. | 260/471 |
| 3,843,647 | 10/1974 | Buzas et al. | 260/247.2 |
| 3,856,857 | 12/1974 | Beregi et al. | 260/553 |
| 3,886,195 | 5/1975 | Beregi et al. | 260/465 |
| 3,956,501 | 5/1976 | Beregi et al. | 424/282 |
| 4,025,624 | 5/1977 | Alphin et al. | 424/233 |
| 4,115,587 | 9/1978 | Lunsford et al. | 424/324 |
| 4,237,165 | 12/1980 | Duhault | 424/308 |
| 4,857,553 | 8/1989 | Ward et al. | 514/557 |
| 4,999,382 | 3/1991 | Wurtman et al. | 514/646 |

FOREIGN PATENT DOCUMENTS

| | | |
|---|---|---|
| 1802297 | 7/1969 | Germany. |
| WO85/05617 | 12/1985 | WIPO. |
| WO88/04552 | 6/1988 | WIPO. |
| WO89/03692 | 5/1989 | WIPO. |
| WO89/09051 | 10/1989 | WIPO. |
| WO90/04387 | 5/1990 | WIPO. |
| WO91/18592 | 12/1991 | WIPO. |

OTHER PUBLICATIONS

Appel, N. M. et al., "Effects of High–Dose Fenfluramine Treatment on Monoamine Uptake Sites in Rat Brain: Assessment Using Quantitative Autoradiography," *Synapse*, vol. 6, pp. 33–44, (1990).

Beckett, A. H. and G. R. Jones, "Metabolic oxidation of aralkyl osimes to nitro compounds by fortified 9000g liver supernatants from various species," *J. Pharm. Pharmac.*, vol. 29, pp. 416–421 (1977).

Coquerel, G., "Interactions during crystallization between enantiomers of norfenfluramine dichloroacetamide (DICAMIDNF)," *Journal of Crystal Growth*, vol. 98, pp. 853–854 (1989).

Coquerel, G. et al., "Optical resolution of (±)–N–Acylnorfenfluramine derivatives by preferential crystallization," *Tetrahedron Letters*, vol. 31, No. 15, pp. 2143–2144 (1990).

Coquerel, G. et al., "Structure of (R)–Nonfenfluramine Dichloroacetate," *Acta Cryst.*, vol. C44, Part 6, pp. 1017–1020 (15 Jun. 1988).

Dunn, R. I. et al., "A novel activity cage for rats: characterization of some phenylethylamine derivatives," *Clinical and Experimental Pharmacology Physiology*, vol. 5, pp. 627–633 (1978).

Elmaleh, D. R. et al, "The in–vivo behavior of D–and L–[C–11]–N–methylnorfenfluramine as serotonin reuptake ligands in rats and monkeys," Abstract No. 03124, The Society of Nuclear Medicine 40th Annual Meeting, Toronto, Canada: 8 Jun.–11 Jun. 1993.

Elmaleh, D. R. et al, "[$^{11}$C]–N–Methyl and Ethyl Nor–Fenfluramine as Serotonin Ligands for Pet," *IXth International Symposium on Radiopharmaceutical Chemistry*, Paris, France, 6–10 Apr. 1992.

Fuller, R. W. et al., "Effect of nonfenfluramine and two structural analogues on brain 5–hydroxyindoles and serum prolactin in rats," *J. Pharm. Pharmacol.*, vol. 34, pp. 449–450 (1982).

Garattini, S. et al., "Progress report on the anorexia induced by drugs believed to mimic some of the effects of serotonin on the central nervous system," *Am J Clin Nutr*, vol. 55, pp. 160S–166S, (1992).

Gardier, A. M. et al., "Autoreceptor Control of Changes in Brain Serotonin Release and Metabolism Induced by Repeated Administration of High Doses of Anorectic Serotoninergic Drugs," *Brain Research* (In Press).

Gobbi, M. et al., "In–vivo (+)–[$^3$H]Fenfluramine Binding to Rat Brain: Biochemical and Autoradiographic Studies," *J. Pharm. Pharmacol.*, vol. 41, pp. 253–256 (1989).

Gray, N. M. et al., "The effects of stereoisomers of 2–amino–6(7)–and 9–amino–6–trifluoromethylbenzonorbornenes on food intake, brain serotonin concentration, and monoamne oxidase activity in the rat," *Pharmacological Research Communications*, vol. 16, No. 3, pp. 281–294.

Grunewald, G. L. et al., "Binding Orientation of Amphetamine and Norfenfluramine Analogues in the Benzonorbornene and Benzobicyclo[3.2.1]octane Ring Systems at the Active Site of Phenylethanolamine N–Methyltransferase (PNMT)," *J. Med. Chem.*, vol. 30, pp. 2191–2208 (1987).

Grunewald, G. L. et al., "Synthesis of Conformationally Defined Analogues of Norfenfluramine. A Highly Stereospecific Synthesis of Amines from Alcohols in the Benzobicyclo[2.2.1]heptene System," *J. Org. Chem.*, vol. 48, pp. 2321–2327 (1983).

(List continued on next page.)

Primary Examiner—Joseph McKane
Attorney, Agent, or Firm—Beth E. Arnold, Esq.

[57] ABSTRACT

Novel meta substituted arylakylamine compounds are disclosed. These compounds can be administered as small molecule drugs to treat diseases or conditions associated with insufficient serotonin mediated nerve transmission (e.g. depression and obesity).

9 Claims, 1 Drawing Sheet

OTHER PUBLICATIONS

Lafferrere, B. and R. J. Wurtman, "Effect of D–fenfluramine on serotonin release in brains of anaesthetized rats," *Brain Research*, vol. 504, pp. 258–263 (1989).

Meng, X. et al., "[C–11]–N–Methyl and Ethyl Nor–Fenfluramine as a Serotonin Ligands for pet" Abstract No. 03085, The Society of Nuclear Medicine 39th Annual Meeting, Los Angeles, CA: 9 Jun.–12 Jun. 1992.

Meng, X. et al, "[I–125]–N–(E)–3–Iodo–Allyl–D(L) Norfenfluramine," Abstract No. 03134, The Society of Nuclear Medicine 40th Annual Meeting, Toronto, Canada: 8 Jun.–11 Jun. 1993.

Meng, X. et al., "The synthesis and labeling of [$^{11}$C]–N–methyl and ethyl nor–fenfluramine as a serotonin ligands for pet," Abstract No. 03085, The Society of Nuclear Medicine 39th Annual Meeting, Los Angeles, CA: 9 Jun.–12 Jun. 1992.

Mennini, T. et al., "Characterization of high affinity and stereospecific [$^3$H]d–fenfluramine binding to rat brain," *Neurochem. Int.*, vol. 13, No. 3, pp. 345–351 (1988).

Offermeir, J. and B. Potgieter, "Some effects of fenfluramine and its derivatives on the central catecholaminergic systems of mice," *Postgraduate Medical Journal*, vol. 51 (Suppl. 1), pp. 65–71, (1975).

Pritchard P. H. and D. N. Brindley, "Studies on the ethanol–induced changes in glycerolipid synthesis in rats and their partial reversal by N–(2–benzoyloxyethyl) norfenfluramine (benfluorex)," *J. Pharm. Pharmac.*, vol. 29, pp. 343–349 (1977).

Ricaurte, G. A. et al., "Dexfenfluramine neurotoxicity in brains of non–human primates," *The Lancet*, vol. 338, pp. 1487–1488 (14 Dec. 1991).

Sarkissian, C. F. et al., "Effects of fluoxetine or D–fenfluramine on serotonin release from, and levels in, rat frontal cortex," *Brain Research*, vol. 529, pp. 294–301 (1990).

Scheffel, U. and G. A. Ricaurte, "Paroxetine as an in vivo indicator of methylenedioxymethamphetamine neurotoxicity: a presynaptic serotonergic positron emission tomography ligand?" *Brain Research*, vol. 527, No. 1, pp. 89–95 (1990).

Zwarenstein, H. and N. Sapeika, "Effect of a norfenfluramine derivative (S780) on NADH dehydrogenase and on certain other enzymes of mouse tissue homogenates," *Research Communications in Chemical Pathology and Pharmacology*, vol. 5, No. 1, pp. 233–236, Jan. (1973).

META SUBSTITUTED ARYLALKYLAMINES AND THERAPEUTIC AND DIAGNOSTIC USES THEREFOR

RELATED APPLICATIONS

This application is a continuation-in-part of U.S. patent application Ser. No. 08/265,512 filed on Jun. 24, 1994, now abandond which itself is a continuation-in-part of U.S. patent application Ser. No. 08/254,032 filed on Jun. 3, 1994 now abandoned.

BACKGROUND OF THE INVENTION

Chemical transmitters are small molecules or pepfides that are synthesized in neurons. There are eight classical and generally accepted low-molecular weight transmitter substances: acetylcholine, dopamine, norepinephrine, serotonin, histamine, glycine, glutamate and γ-aminobutyric acid (GABA). The catecholamines, dopamine, norephinephrine and epinephrine (derived from the amino acid tyrosine), the indolamine, serotonin, (derived from the amino acid tryptophan) and histamine (an imidazole) together comprise the "biogenic amines".

In response to an appropriate stimulus, chemical transmitters are released into a synaptic cleft (gap) where they either bind to a postsynaptic neuron or effector organ; or are removed. There are three mechanisms by which nervous tissue disposes of soluble or unbound transmitter substances: 1) diffusion, 2) enzymatic degradation (e.g. monoamine oxidases degrade biogenic amines); and 3) reuptake by high affinity, chemical transmitter specific uptake mechanisms.

The chemical transmitter serotonin is known to mediate stimulation or inhibition of a variety of smooth muscles and nerves, thereby influencing secretion by exocrine and endocrine glands and functioning of the respiratory, cardiovascular and central nervous systems. Serotonergic neurons are known to be involved in control of sleep, appetite, nutrient selection, blood pressure, mood, endocrine secretion, aggressivity, and numerous other sensitivities to external stimuli.

Certain chemicals or drugs are known to affect serotonin level or activity, thereby producing a therapeutic effect. For example, it has been found that endogenous serotonin levels can be increased by administering its precursor tryptophan. In addition, the drugs fluoxetine (Prozac) and trazodone are thought to increase the availability of serotonin in the presynaptic cleft by blocking its reuptake by presynaptic neurons. These drugs have shown clinical utility for treating depression and stimulating weight loss. Two other "serotonin uptake blockers", fenfluramine and its principal metabolite norfenfluramine, have also shown clinical utility in treating depression and obesity. In addition to blocking the uptake of serotonin by postsynaptic neurons, norfenfluramine appears to enhance serotonin release from presynaptic vessicles.

Although serotonin uptake blockers are considered the most effective class of antidepressants (when compared to monoamine oxidase inhibitors such as phenelzine, and tricyclic compounds, such as imipramine and amitriptyline), currently available compounds have associated side effects. For example fluoxetine (Prozac®) has been linked to aggressive behavior.

New compounds that increase the availability of serotonin at serotonergic neuronal gap junctions in vivo would be useful for treating a variety of diseases and conditions associated with inadequate serotonin-mediated nerve transmission.

SUMMARY OF THE INVENTION

In one aspect, the instant invention features novel meta substituted arylalkylatnines having a high specificity for serotonergic neurons. Preferred meta substituted arylalkylamines are readily taken up by the central nervous system and peripheral organs innervated by serotonergic neurons. Other preferred meta substituted arylalkylamines bind with high affinity to serotonergic neurons.

In another aspect, the invention features small molecule drugs comprised of the novel meta substituted arylalkylamine compounds. The invention further features therapeutic uses for the novel small molecules for treating or preventing a condition or disorder associated with inadequate serotonin mediated nerve transmission. In preferred embodiments, the disease or condition is depression or obesity. In a preferred method for treating obesity, the pharmaceutical composition is administered in conjunction with a thermogenic drug.

In a further aspect, the instant invention features labeled meta substituted arylalkylamines and uses for the labeled compositions. In one embodiment, labeled meta substituted arylalkylamines can be administered in vivo or in vitro and monitored by a means appropriate for the label to measure the binding of serotonin or a serotonin ligand to serotonergic neurons. Preferred methods for monitoring labeled meta substituted arylalkylamines in vivo include Positron Emission Tomography (PET), Single Photon Emission Computer Tomography (SPECT) or Magnetic Resonance Imaging (MRI).

The instant disclosed small molecules are readily taken up in vivo by serotonergic neurons of the central nervous system (i.e the brain and spinal cord) and peripherally in heart, lung, liver, spleen, kidney and adrenal glands. These small compounds should therefore be safe and effective therapeutic agents. In addition, certain of the compounds have a high affinity for serotonergic neurons. These compounds should be especially potent therapeutics and if labeled, useful imaging agents. Further, some of the compounds are more resistant to in vivo catabolism (e.g. by monoamine oxidase) requiring a low dose to yield a therapeutic effect. The instant disclosed small molecule drugs therefore should result in few, if any, side effects. In addition, the structure of the compounds indicate that meta substituted arylalkylamines (unlike amphetamines, which are not meta substituted) should be nonaddictive drugs.

Additional features and advantages of the invention will become more apparent from the following detailed description and claims.

BRIEF DESCRIPTION OF THE FIGURES

The Figure shows a schematic method for synthesizing and resolving β-methyl-3-trifluoromethyl phenylethylamine into D (+) and L (−) enantiomers.

DETAILED DESCRIPTION OF THE INVENTION

Lipophilic Phenylethylamines

Figure 1:
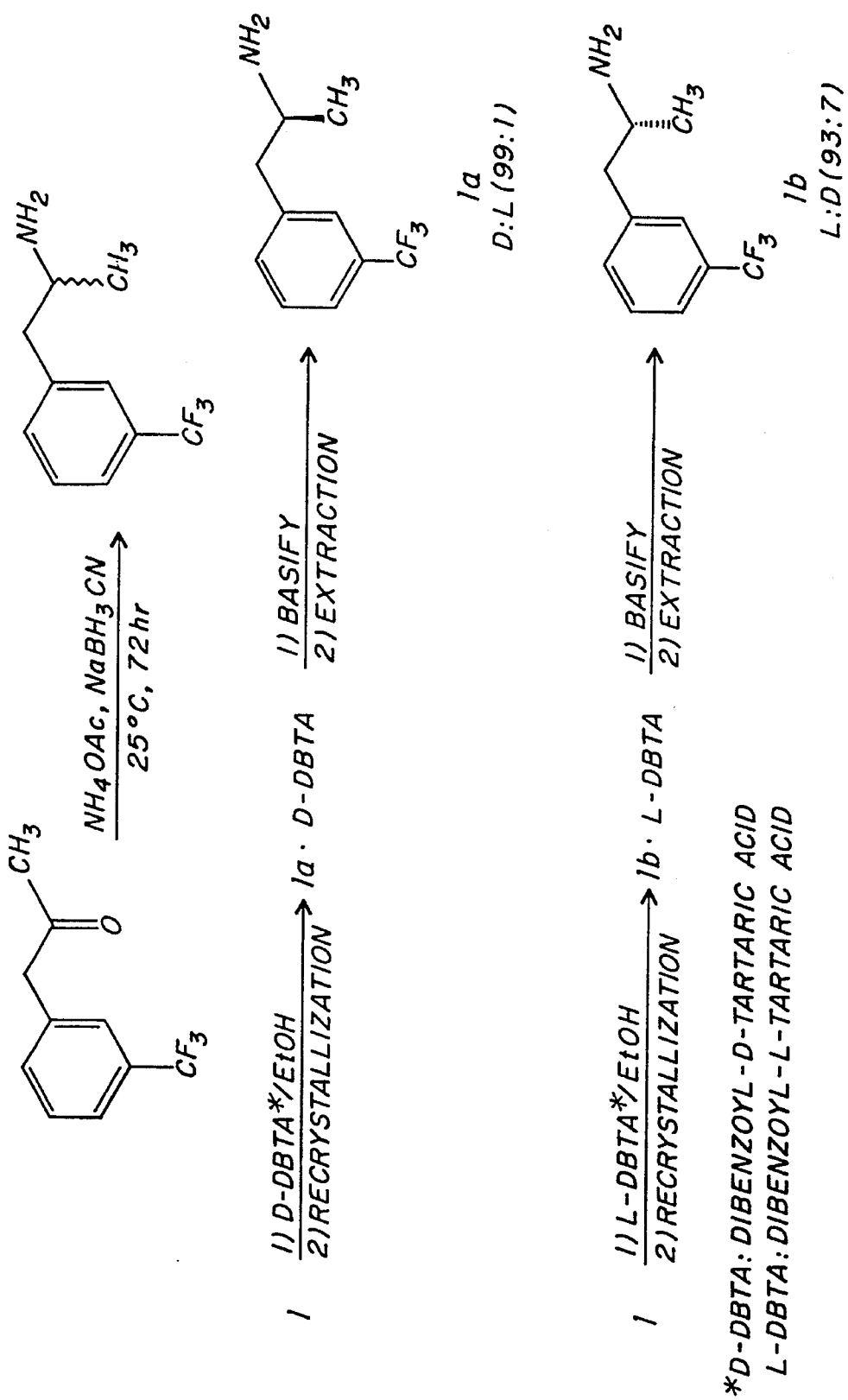

In one embodiment, the meta substituted arylalkylamines of this invention are D (+) or L (−) enantiomers of the following structural formula:

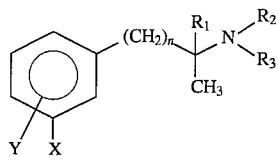

wherein,

X=CF$_3$, CH$_3$, C$_2$H$_5$ or CCl$_3$;

Y=Cl or Br; ortho, para or meta to X;

n=1, 2 or 3;

R$_1$=H and R$_2$ and R$_3$=acyl, alkylene, alkenylene, alkynylene, alkenyl and alkynyl groups; or R$_1$=CH$_3$ and R$_2$ and R$_3$=H, acyl, alkylene, alkenylene, alkynylene, alkenyl and alkynyl groups In another embodiment, the compounds are D (+) or L (−) isomers of the formula:

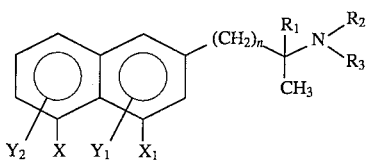

wherein

X=H and X$_1$=CF$_3$, CH$_3$, C$_2$H$_5$, CCl$_3$; or

X$_1$=H and X=CF$_3$, CH$_3$, C$_2$H$_5$, CCl$_3$;

Y$_1$=Cl or Br ortho, para or meta to X;

Y$_2$=Cl or Br ortho, para or meta to X;

n=1, 2 or 3; and

R$_1$=H and R$_2$ and R$_3$=acyl, alkylene, alkenylene, alkynylene, alkenyl and alkynyl groups or R$_1$=CH$_3$ and R$_2$ and R$_3$=H, alkyl, alkylene, alkenylene, alkynylene, alkenyl and alkynyl (e.g. vinyl

or propargyl

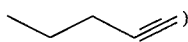)

In a further embodiment, the compounds are D (+) or L (−) enantiomers of the formula:

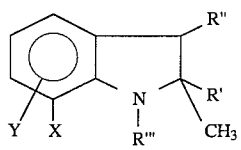

wherein,

R'=H or CH$_3$;

R"=H, acyl, alkyl or

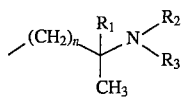

R'''=acyl, alkyl, alkylene, alkenylene, alkynylene, alkenyl and alkynyl (e.g. vinyl

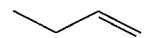

or propargyl

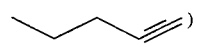)

n=1, 2 or 3; and

R$_1$=H and R$_2$ and R$_3$=alkylene, alkenylene, alkynylene, alkenyl and alkynyl groups or R$_1$=CH$_3$ and R$_2$ and R$_3$=H, alkyl, alkylene, alkenylene, alkynylene, alkenyl and alkynyl groups.

The alkylene, alkenylene, alkynylene, alkenyl and alkynyl groups (hereinafter hydrocarbon groups) comprising the R groups can be either straight or branched chains, saturated or unsaturated. Unsaturated groups may have a single site of unsaturation or a plurality of unsaturated sites. The hydrocarbon groups preferably have up to about ten carbons, more preferably up to about six carbons, and most preferably up to about three carbons. A hydrocarbon group having three carbon atoms or less is considered to be a lower hydrocarbon group. For example, an alkyl group having three carbon atoms or less is a lower alkyl. Examples of lower hydrocarbon groups which may be used in the present invention include methyl, methylene, ethyl, ethylene, ethenyl, ethenylene, ethynl, ethynylene, propyl, propylene, propenyl, propenylene, propynyl, and propynylene. Examples of higher hydrocarbon groups (from four to about ten carbons) include butyl, t-butyl, butenyl, butenylene, and butynyl, butynylene, nonyl, nonylene, nonenyl, nonenylene, nonynyl, and nonynylene.

The alkyl or alkylene groups may be substituted with one or more oxygen or halogen atom to form alkoxy, haloalkyl, alkoxyene, and haloalkylene groups. The alkoxy and haloalkyl groups also may be straight or branched chain and preferably are made up of up to about ten atoms (including carbon, oxygen or halogen), preferably up to about six atoms, and most preferably up to about three atoms. The term halogen is art-recognized and includes chlorine, fluorine, bromine, and iodine. Examples of substituted hydrocarbon groups which are useful within this invention are similar to hydrocarbon groups set forth above except for the incorporation of oxygen(s) or halogen(s) into the groups. Because the alkoxy, haloxy, alkoxyene and haloalkylene compounds will be less lipophilic, they may not act as serotonin agonists as described below, but instead prove to be serotonin antagonists or dopamine agonists when administered to a subject in vivo.

Preferred compounds include D and L enantiomers of N-methyl-β-methyl-3-trifluorophenylethylamine; N-3-iodopropyl-2-nyl-β-methyl-3-trifluorophenylethylamine; N-3-(E)-tributyl-propyl-2-nyl-β-methyl-3 trifluorophenylethylamine and N,N-dimethyl-β-methyl-3-trifluorophenylethylamine which can be made as specifically described in the following Example 1.

In addition to the synthesis procedures set forth in Example 1, compounds wherein R$_1$=H in the structural formula can be prepared by reacting the corresponding aryl, ketone precursor with sodium borocyanide in the presence of ammonium acetate to provide the primary amines. The primary amines can be resolved by chiral HPLC or by recrystallization with D or L known salts as shown schematically in FIG. 1 for resolution of N-methyl-β-methyl-3-trifluorophenylethylamine.

A series of arylalkylamines (R$_1$=CH$_3$) can be prepared by reacting the corresponding arylalkyl acids with thionylchloride in ethanol to yield the ethylester. The ester reaction with an alkyl Grignard will afford the tertiary alcohol. A further reaction with NaCN and concentrated sulfuric acid in glacial acetic acid (A Ritter reaction) yields the N-formyl derivative. Hydrolysis in ethanolic hydrogen chloride produces the primary amine. Reduction of the N-formyl derivatives with lithium aluminum hydride will provide the N-methyl arylalkylamines. Further reactions with alkyl-iodides will provide a variety of compounds.

Synthesized meta substituted arylalkylamine compounds can be characterized using standard methods of high field NMR spectra as well as IR, MS and optical rotation. Elemental analysis, TLC and/or HPLC can be used as a measure of purity. A purity of>98% is preferred. TLC and/or HPLC can also be used to characterize more lipophilic compounds.

Meta substituted arylalkylamine compounds can be prepared as free bases or salts, (e.g., the naphthalene-1,5-disulfonate, tartrate or hydrochloride salts). A reaction of the free amine with the corresponding acid will provide the required salt.

Once prepared, candidate meta substituted arylalkylamine compounds can be screened for ability to bind serotonergic neurons e.g., by administering labeled compound into a subject and monitoring in vivo (e.g. as described in the attached Example 2) or in vitro binding (e.g. as described by Madras et al., (1989) *Mol. Pharmacol.* 36:518–524). And/or, a particular meta substituted arylalkyl amine compound can be tested for selectivity and tissue uptake as described in the attached Example 3.

Therapeutic Uses for Meta Substituted Arylalkylamines

Meta substituted arylalkylamines are thought to specifically bind serotonergic neurons in a manner that blocks "reuptake", resulting in increased availability for binding to serotonergic receptors on postsynaptic neurons. This proposed mechanism of action is based to some degree on the similarity in structure between the instant disclosed arylalkylamines and fenfluramine. D-fenfluramine is a halogenated amphetamine which lacks amphetamine's ability to release catecholamines. It's utility as an appetite suppressant and in treating infantile autism is believed to result from its ability to inhibit serotonin's presynaptic reuptake and the ability of its principal metabolite, D-norfenfluramine to enhance serotonin's release (Sarkissian, C.F. et al., Brain Research 529:294–301 (1990); and U.S. Pat. No. 4,999, 382).

Based on the specific binding and mechanism of action of meta substituted arylalkylamines, the instant invention also features a number of therapeutic applications for the novel small molecules. In one embodiment, an appropriate amount of a meta substituted arylalkylamine is administered to a subject to treat or prevent a condition or disorder associated with inadequate serotonin mediated nerve transmission. Examples include depression (unipolar and bipolar as well as depression associated with psychoses and Alzheimer's Disease), as well as obesity. The compounds should also prove useful in treating symptoms associated with inadequate serotonin mediated nerve transmission such as obsessive-compulsive disorders, aberrant eating disorders, Tourette's Syndrome, anxiety, aggression, impulsivity, headaches, migraines, alcohol or drug dependency, pathological crying condition, seasonal effective disorders, panic disorders, as supplement to low calorie diet, menarche, menopause, Post Menstrual Syndrome, pain disorders, trauma, symptoms associated with diabetes, libido dysfunction, and symptoms associated with low serum cholesterol. Also certain compounds may improve cognitive function and mental health. In addition, highly lipophilic compounds, capable of acting as dopamine antagonists would be useful for alleviating the symptoms associated with drug withdrawal. In addition to being administered therapeutically, the compounds can be taken prophylactically to lower the risk of heart disease, cancer or pathogenic infection.

As used herein the term "depression" is a clinical term for an affective disorder encompassing unipolar depression (major depression) and bipolar depression (manic depressive illness) as described e.g. in Kandel, Eric R et al., Principles of Neural Science, 3rd ed., Elsevier, N.Y. 1991 pgs. 870–880. In addition, clinical depression can be associated with other conditions such as Alzheimer's disease, psychotic episodes, aging, cancer and other chronic or terminal diseases.

A "pychoses" or "psychotic episode" refers to a discrete, often reversible mental state, which if untreated may last for many months, in which a patient loses the ability to test reality. Loss of reality testing may be accompanied by other disturbances of higher mental functioning, especially hallucinations, delusions, incoherent thinking, disordered memory and confusion.

Alzheimer's Disease or "Alzheimer's" is a condition characterized by progressive destruction of cholinergic neurons, resulting in reduction of choline acetylesterase activity (up to 90%). Alzheimer's is associated with memory loss, depression and decreased physical activity. Monoamine oxidase inhibitors have shown utility in treating depression in patients with Alzheimer's. Also studies have shown that monoamine oxidase levels increase with age and that patients with dementia have higher levels of monoamine oxidase than age-matched control subjects. These factors support the utility of the instant disclosed small molecule drugs for treating Alzheimer's and associated depression.

Drugs, which have shown utility for treating depression have been shown to act on serotonergic pathways. As discussed in the Background of the Invention, the drugs fluoxetine (Prozac) and trazodone, commonly used in treating depression, are thought to increase the availability of serotonin in the presynaptic cleft by blocking its reuptake by presynaptic neurons. Two other "serotonin uptake blockers", fenfluramine and its principal metabolite norfenfluramine, have also shown clinical utility in treating depression. In addition, the monoamine oxidase inhibitor class of antidepressants (e.g. phenelzine and isocarboxazid) are thought to produce an increased level of serotonin in gap juctions by preventing its degradation by monoamine oxidases.

The term "obesity" refers to a condition characterized by an excess of fat over that needed to maintain health. The pathogenesis of obesity relates to feeding behaviour, body fat storage mechanisms and genetic and psychological influences. In addition certain medications (e.g. steroids, imipramine, trazadone, desipramine and tricyclic compounds) may cause or contribute to obesity. Certain serotonin reuptake inhibitors, such as fluoxetine (Prozac) and fenfluramine (fenfluramine hydrochloride (Pondimin), are known to effect weight reduction. (See for example U.S. Pat. No. 4,999,382).

For use in therapy, an effective amount of a meta substituted arylalkylamine can be administered to a subject by any mode allowing the small molecule to be taken up by the appropriate organ and perform its intended function on serotonergic neurons. Preferred routes of administration include oral and transdermal (e.g. via a patch). Examples of other routes of administration include infection (subcutaneous, intravenous, parenteral, intraperitoneal, intrathecal, etc.). The injection can be in a bolus or a continuous infusion. Depending on the route of administration, the meta substituted arylalkylamine compound can be coated with or disposed in a selected material to protect it from natural conditions which may detrimentally effect its ability to perform its intended function, increase its in vivo availability or increase its uptake by a specific organ.

The small molecule meta substituted arylalkylamines can be administered alone, or in conjunction with a pharmaceutically acceptable carrier. As used herein, the phrase "pharmaceutically acceptable carrier" is intended to include substances that can be coadministered with a meta substituted aryl, alkylamine and allows the small molecule to perform its intended function. Examples of such carriers include solutions, solvents, dispersion media, delay agents, emulsions and the like. The use of such media for pharmaceutically active substances are well known in the art. Any other conventional carrier suitable for use with meta substituted arylalkylamine compounds also falls within the scope of the present invention.

Further, the small molecule drugs can be administered in conjunction with other active agents, for example, in treating or preventing obesity, the small molecules can be co-administered with a thermogenic drug such as ephedrine, xanthine derivative such as caffeine, theophylline, amphetamines and beta agonists (Astrup et al., Am J Clin Nutr (1992 Jan) 55 (1 Suppl):246S-248S). In addition, in treating or preventing depression, the small molecules can be co-administered with antidepressants or other drugs. The meta substituted arylakylamine compounds can be administered prior to, simultaneously or after the administration of the thermogenic drug. The meta substituted arylalkylamine can also be administered as a prodrug which is converted to its active form in vivo.

The language "effective amount" of a meta substituted arylalkylamine compound refers to that amount necessary or sufficient to increase the level of serotonin in serotonergic neuron gap junctions. The effective amount can vary depending on such factors as the disease or condition being treated the stimulant, the particular meta substituted arylalkylamine compound being administered, the size of the subject, or the severity of the disease or condition. One of ordinary skill in the art can empirically determine the effective amount of a particular meta substituted arylalkylamine compound alone or in conjunction with a thermogenic drug or other active agent without necessitating undue experimentation.

Preferred doses for treating obesity are in the range of 0.3–1 mg/kg three times a day. Surprisingly it has been found that administration of lower doses (e.g. in the range of 0.1–0.3 mg/kg once every two days) actually induces weight gain and therefore may be a useful treatment for cachexia, bolemia, anorexia nervosa or other conditions associated with weight loss. Co-administration of the compounds with other drugs may or may not lower the administrated dose.

Radiolabeled Meta Substituted Arylakyl Amines for Nerve Imaging

Meta substituted arylalkylamine compounds can be labeled with a variety of imaging agents, which are known in the art and which will depend to some extent on the means used to detect or monitor the compound in vivo or in vitro. Preferred imaging agents for performing positron emission tomography (PET), single photon emission computer tomography (SPECT) include F-18, Tc-99m, and I-123. Preferred imaging agents for magnetic resonance imaging (MRI) include an appropriate atom with unpaired spin electrons or a free radical. An imaging agent can be complexed with meta substituted arylalkylamine compound by a variety of techniques that are well-known in the art. In a preferred embodiment, the imaging agent is attached to the aryl ring of the meta substituted arylalkylamine. Most preferrably an imaging agent is conjugated to the reactive nitrogen of a meta substituted arylalkylamine.

Meta substituted arylalkylamine compounds that have been labeled with an appropriate imaging agent can be added to in vitro cultures of neurons for determining changes in the brain associated with serotonin nerve transmission and to monitor the binding of serotonin or a serotonin ligand to serotonergic neurons e.g. as described by Madras et al., (1989) *Mol. Pharmacol.* 36:518–524.

Labeled meta substituted arylalkylamines can also be injected into an appropriate subject (e.g. monkey, dog, pig, cow) and its binding with serotonin monitored in vivo (e.g. as described in the following Example 2.

Meta substituted arylalkylamines showing high affinity binding to serotonergic neurons are most useful as imaging probes because they display a low level of nonspecific binding and accumulate in quantity at serotonergic regions.

The present invention is further illustrated by the following examples which should not be construed as limiting in any way. The contents of all cited references (including literature references, issued patents, published patent applications, and co-pending patent applications) cited throughout this application are hereby expressly incorporated by reference.

EXAMPLE 1

SYNTHESIS OF META SUBSTITUTED ARYLALKYLAMINES

All reagents and solvents were purchased from Aldrich Chemical Company and were used without further purification. Lithium aluminum hydride and tetrahydrofuran (THF) were purchased from Fluka Chemical Company and used without further purification. Melting points were measured with a Fisher-Johns melting point apparatus and are uncorrected. NMR spectra were recorded with a Bruker Am500 instrument using $CHCl_3$-$d_3$ as solvent and TMS as an internal standard. A scanditronix MC-17 cyclotron and RB-86 automatic chemical production robotic system were used for preparation of [$^{11}$C] methyl iodide. Elemental analysis for carbon, hydrogen and nitrogen was performed by Galbraith Laboratories, Inc., Knoxville, Tenn. Silica gel Gf254 plates from Analtach, Inc., were used for thin layer chromatography, and alumina (neutral, III) for column chromatography was purchased from Aldrich Chemical Company.

(D,L (±)β-methyl-3-trifluorophenylethylamine (norfenfluramine)

To a 500 ml, one-necked, round-bottomed flask equipped with a nitrogen inlet was added 6.07 g (30 mmol) of 3-trifluoromethylphenylacetone, 150 mL of dry 2-propanol, 10.1 g (141 mmol) of ammonium acetate, 8 g of 3A molecular sieves and 1.98 g of sodium cyanoborohydride. The resulting suspension was stirred at room temperature for 72 hours. The reaction mixture was then diluted with 500 mL of methanol and filtered. The filtrate was concentrated to a syrup, to which was added 250 mL of methylene chloride and 150 mL of 15% aqueous sodium hydroxide. After separation, the aqueous layer was extracted with methylene chloride (4×100 mL). The combined organic phase was washed with 100 mL of water, 100 mL of saturated sodium chloride solution, then dried over magnesium sulfate. The solvent was removed under reduced pressure to give a pale yellow oil (5.93 g). Silica gel TLC showed a major spot with Rf value 0.38 ($CH_2Cl_2$: MeOH: $Et_3N$ 9:1:0.1). Alumina column chromatography ($CH_2Cl_2$) was used for the purification to give 5.22 g (yield 86%) of pure racemic β-methyl-3-trifluorophenylethylamine free base. 1H NMR($CDCl_3$) (ppm) 7.35–7.47(4H,m, Ar-H), 3.19 (1H,m, CH), 2.74 (1H, dd,J=13.3, 5.5 Hz, HCH), 2.58 (1H, dd,J=13.3, 7.9 Hz, HCH), 1.27 (2H, br.s, disappeared with $D_2O$ exchange, $NH_2$), 1.10 (3H, d,J=6.3 Hz, $CH_3$). (±)-β-methyl-3-trifluorophenylethylamine hydrochloride was prepared by passing a stream of dry hydrogen chloride gas through a solution of (±)-β-methyl-3-trifluorophenylethylamine in ether (2.0M) and recrystallized from ethanol-ether, colorless needles, mp 173–174.50.

D (+) β-methyl-3-trifluorophenylethylamine 2.09 g of racemic β-methyl-3-trifluorophenylethylamine free base was added to a solution of anhydrous dibenzoyl-D-tartaric acid (3.5 g) in 40 mL of anhydrous boiling ethanol. The mixture was cooled to room temperature and slow crystallization gave the dibenzoyltartarate as a white crystalline compound (1.44 g). Recrystallization from anhydrous methanol (30 mL) gave a fine crystalline product (0.55 g) mp 200° dec. The dibenzoyl-D-tartarate was basified with 4N aqueous sodium hydroxide (10 mL) followed by extraction with methylene chloride (3×15 mL) to liberate (+)-β-methyl-3-trifluorophenylethylamine free base as a very pale yellow oil (135 mg), [α]=+21.1° (C=EtOH) [ref.[α]=+21.5° (C=8.0, EtOH) (18)].

L (−) β-methyl-3-trifluorophenylethylamine 2.64 g of racemic β-methyl-3-trifluorophenylethylamine was slowly added to a solution containing dibenzoyl-L-tartaric acid (4.65 g) in 30 mL of anhydrous boiling ethanol. At the end of addition, the mixture was cooled to room temperature. Filtration provided 3.63 g of a white powder. Recrystallization from 75 mL of an hydroxide methanol gave 0.75 g of fine prisms. The crystalline salt was treated with 4N aqueous sodium hydroxide (10 mL) and then extracted with methylene chloride (3×15 mL) to give 230 mgs. of L(−)β-methyl-3-trifluorophenylethylamine free base as a pale yellow oil ct α=−20.5° (EtOH).

(±)-N-Methyl-β-methyl-3-trifluorophenylethylamine

The procedure for preparation of (±)-N-methyl-β-methyl-3-trifluorophenylethylamine was similar to that used for (±)β-methyl-3trifluorophenylethylamine. A mixture of a 3-trifluoromethylphenylacetone (6.07 g, 30 mmol), methylamine hydrochloride salt (10.0 g, 150 mmol), sodium cyanoborohydride (1.98 g 30 mmol), 3A molecular sieves (8.0 g) and 160 mL of 2-propanol was stirred under nitrogen at room temperature for 48 hours. After work-up and purification in the same manner as for (d, 1)-β-methyl-3-trifluorophenylethylamine, 5.48 g of pure (±)-N-methyl-β-methyl-3-trifluorophenylethylamine was obtained (yield 85.8) as a pail yellow oil. $^1H$ NMR ($CDCl_3$)s(ppm) 7.35–7.46 (4H, m, Ar-H), 2.80 (2H, m, CH, HCH), 2.62 (1H, m, HCH), 2.41 (3H, S, N-$CH_3$), 1.30 (1H, brd.s, disappeared with $D_2O$ exchange, NH), 1.03 (3H,d,J=6.1 Hz, $CH_3$). $^{13}CNMR$ (125 MHz,$CDCl_3$, proton decoupling)s(ppm) 140.5, 132.8, 128.8, 126.0, 123.1, 56.3, 43.3, 34.1, 19.7. The hydrochloride salt of (±)N methyl-β-methyl-3-trifluorophenylethylamine was collected as colorless needles from ethyl acetate,mp.

Elemental analysis found: C 51.97%, H 5.97%; calculated: C 52.08%, H 5.96% , N 5.22%.

[$^{11}C$]-N-methy-(±)-β-methy-3-trifluorophenylethylamine

[$^{11}C$]-$CO_2$ was produced by nuclear reaction $^{14}N$(p, n) $^{11}C$ in the cyclotron and collected in a copper coil in liquid nitrogen. It was then transferred through a calcium chloride drying tube into a reaction vial containing 0.5 mL of 0.1M solution of lithium aluminum hydride (LAH) in tetrahydrofuran (THF). After the [$^{11}C$]-$CO_2$ transfer was completed, the THF solution was evaporated by heating the reaction mixture at 120°[$^{11}C$]-Methyl iodide (MeI) was generated by adding 0.5 mL of 57% aqueous hydroiodic acid to the $LiA1(O^{11}CH_3)_4$ complex and distilling [$^{11}C$]-MeI through an asearite drying tube. [$^{11}C$]-MeI was collected in a separate reaction vial which contained 100 ug of (±)-β-methyl-3-trifluorophenylethylamine precursor and 100 uL of solvent mixture of acetonitrile: N,N-dimethylformate (DMF) (9:1) at 0°–5°. The reaction mixture was heated at 120° for 5 minutes and the solvents were removed by blowing a nitrogen stream into the vial. The residue was dissolved in 3 mL of Lactate Ringer injection solution (pH=6.5) and filtered through a Millipore filter (0.22μ). This final solution was used for animal study without further purification. Radiochemical purity was shown to be 99% by radio TLC scanning (silica gel aluminum backed plate, $CH_2Cl_2$: MeOH: $Et_3N$ 9:1:0.1, Rf=0.35). Radiochemical yield was 6–8% and the specific activity was over 400 mCi/umol as determined by HPLC.

D-N-3-Iodo-propyl-2-nylβ-methyl-3-trifluorphenyethylamine

A mixture of 203 mg(10 mmol) of D β-methyl-3-trifluorophenylethylamine, 365 mg (1.0 mmol) of 3-(E)-tributylstanyl-propyl-2nyl-chloride, 17 mg (0.1 mmol) of potassium iodide, 138 mg (1.0 mmol) of potassium carbonate and 10 mL of dry-DMF was heated at 75°–80° C. for 20 hrs. The reaction mixture was partionized by 20 mL of water and ethyl acetate (1:1 v/v). The ethyl acetate layer was separated and aqueous layer was extracted with ethyl acetate (2×15 mL). The combined organic phase was washed with water (10 mL) saturated sodium chloride solution and dried over magnesium sulfate. After a column chromatographic (silica gel, hexane: ethyl acetate:triethylamine 10:1:0.1 v/v)4 separation 200 mg of pure (±)N-3-(E)-tributyl-propyl-2-nyl-β-methyl-3-trifluorophenylethylamine was obtained as a pale yellow oil TLC (silica gel plate, Hexane:EtOAc =2:2:0.01), Rf=0.3 yield 37.6% 7.52–7.37 (4H, m, $C_6H_4$) 6.73 (1H,dt, J=14.0, 6.0 Hz, C=(HR), 5.89 (1H,d,J=14.0 Hz, C=CHI) 4.40 (1H,dd,J=14.0, 6.0 Hz, HCH-C=C), 3.88 (1H,dd,J= 14.0, 6.0 Hz,3.45 (1H,m,CH), 2.80 (2H,m, $C_6H_4CH_2$) 1.01–1.59 (27H,m.3×$CH_3CH_2CH_2CH_2$) 1.06 (3H,d J=6 Hz $CH_2CH_3$).

D(+)N-3-(E)-tributyl-propyl-2-nyl β-methyl-3-trifluorophenylethylamine

The compound has been made by the same procedure as used for racemic product yield 60% (0.5 mmol scale) (±)-N-3-(E)-tributylstanyl-propyl-2-nyl-β-methyl-3-trifluoropheny ethylamine. The synthetic procedure is the same as for (+)N-3-(E)-tributylpropyl-2-nyl-β-methyl-3-trifluorophenylethylamine (0.2 mmol scale) Yield 43.7%.

(±) N-3(E)-iodo-propyl-2-nyl-β-methyl-
3-trifluorophenylethylamine 190 mg (0.30 mmol) of (±) N-3(E)-tributylstanyl-propyl-2-nyl-β-methyl-3-trifluorophenylethyl amine was dissolved in 1 mL of methylene chloride and added with saturated $I_2/CH_2Cl_2$ solution at 25° C. until the reaction mixture turned pale yellow. The reaction mixture was then washed with 3 mL of saturated sodium bisufite, dried over magnesium sulfate. After the solvent was removed under reduced pressure and residue was applied to column chromatographic separation (silica gel, $CH_2Cl_2$), 102 mg of pure iodo compound was obtained as a colorless syrup yield 77% $^1$HNMR(500MHz, $CDCl_3$)(m): 7.50–7.36 (4H,m,$C_6H_4$); 6.57 (1H,dt, J=145, 5.7 Hz, C=CHR); 6.25($H_6$,d,J=14.5, C=CHI); 3.30 (1H,m,C); 2.84 (1H,dd,J=13.4 6.1 Hz 2.67 (1H,dd,J=13.4, 7.0 Hz, $C_6H_4CH_2$ 1.25 (1H, S,NH); 1.07 (3H,d,J=6.2 Hz,$CH_3$).

(+) or (−) N-3 (E,Z)-iodo-propy-2-nyl-β-methyl-
3-trifluorophenylethylamine (+) or (−) N-3 (E,Z)-iodo-propyl-2-nyl-β-methyl-3-trifluorophenylethylamine can be made by the same procedure used for racemic iodo compound.

EXAMPLE 2

Position Emission Tomography (PET) Imaging of Carbon-11-Labeled D-
N,N-dimethyl-β-methyl-3-trifluorophenyethylamine
In Rat And Monkey Brain D(+) or L (−) N,N-dimethyl-β-methyl-3-trifluorophenyethylamine was prepared by reacting the monomethyl derivative with lower molar amounts of methyl iodide in acetonitrile. Five to ten mCi of Carbon-11-labeled D N,N-dimethyl-β-methyl-3-trifluorophenyethylamine was injected IV into a cytomologous monkey. The images obtained were coronal levels collected 30 mins. after IV injection. Brain areas such as caudate, putamen, thalamus, hypothalamus, and frontal cortex showed highest levels of activity.

Table 1 shows the distribution of I-125 labelled L(E)-iodoally β-methyl-3-trifluorophenyethylamine in rat brain as percent injected dose per gram of tissue and per organ. The brain distribution is given for uptake in the hypothalamus, cerebellum, pons, cortex, thalamus and striatum at 5, 30 and 60 minutes.

TABLE I

Distribution of I-125 In Rat Brain Following Injection Of
I-125 Labeled L(E)-Iodoallyl-β-methyl-3-triflorophenyethylamine

|  | 5 Minutes | 30 Minutes | 60 Minutes |
| --- | --- | --- | --- |
| Hypothalamus | 0.64 ± 0.12 | 0.21 ± 0.04 | 0.15 ± 0.11 |
| Cerebellum | 0.64 ± 0.08 | 0.20 ± 0.02 | 0.10 ± 0.02 |
| Pons | 0.65 ± 0.09 | 0.20 ± 0.03 | 0.12 ± 0.01 |
| Cortex | 0.67 ± 0.10 | 0.21 ± 0.02 | 0.10 ± 0.02 |
| Thalamus | 0.74 ± 0.06 | 0.24 ± 0.03 | 0.13 ± 0.01 |
| Striatum | 0.63 ± 0.08 | 0.21 ± 0.03 | 0.09 ± 0.02 |

(Distribution data obtained from six rats is reported as average percent of injected dose, plus or minus standard deviation.)

Table 2 shows the distribution of I-125 labelled D(E)-iodoallyl-β-methyl-3 trifluorophenyethylamine in rat brain as percent injected dose per gram of tissue and per organ. The brain distribution is given for uptake in the hypothalamus, cerebellum, pons, cortex, thalamus and striatum at 5, 30 and 60 minutes.

TABLE 2

Distribution Of I-125 In Rat Brain Following Injection Of I-125
Labelled D(E)-Iodoallylβ-methyl-3-trifluorophenyethylamine

|  | 5 Minutes | 30 Minutes | 60 Minutes |
| --- | --- | --- | --- |
| Hypothalamus | 1.53 ± 0.19 | 1.36 ± 0.31 | 1.00 ± 0.10 |
| Cerebellum | 1.65 ± 0.15 | 1.43 ± 0.21 | 1.11 ± 0.16 |
| Pons | 1.77 ± 0.10 | 1.50 ± 0.28 | 1.08 ± 0.15 |
| Cortex | 1.92 ± 0.16 | 1.39 ± 0.20 | 1.00 ± 0.12 |
| Thalamus | 1.80 ± 0.17 | 1.51 ± 0.21 | 1.25 ± 0.20 |
| Striatum | 1.67 ± 0.16 | 1.25 ± 0.17 | 1.00 ± 0.19 |

(Distribution data obtained from six rats is reported as average percent of injected dose, plus or minus standard deviation.)

High extraction of activity was observed with the D enantiomer in all of the brain tissue tested. The thalamus showed the highest uptake. The activity at 60 minutes decreased by 30% where the L enantiomer showed lower uptake and faster washout from the brain regions.

TABLE 3

Distribution Of I-125 In Rat Tissue Following Injection Of I-125
Labeled D(E)-Iodoallyl-β-methyl-3-trifluorophenyethylamine

|  | 5 Minutes | 30 Minutes | 60 Minutes |
| --- | --- | --- | --- |
| Blood | 0.62 ± 0.03 | 0.59 ± 0.06 | 0.58 ± 0.06 |
| Heart | 1.47 ± 0.11 | 0.68 ± 0.07 | 0.46 ± 0.04 |
| Lung | 6.88 ± 0.30 | 3.03 ± 0.37 | 1.75 ± 0.20 |
| Liver | 1.47 ± 0.25 | 1.46 ± 0.26 | 1.22 ± 0.20 |
| Spleen | 1.74 ± 0.42 | 1.58 ± 0.21 | 1.14 + 0.18 |
| Kidney | 2.85 ± 0.43 | 1.50 ± 0.18 | 1.04 + 0.12 |
| Adrenal | 1.99 ± 0.37 | 1.00 ± 0.16 | 1.16 + 0.25 |
| Stomach | 0.80 ± 0.11 | 4.48 ± 0.83 | 4.40 + 0.65 |
| Muscle | 0.70 ± 0.09 | 0.60 ± 0.14 | 0.32 + 0.60 |

(Distribution data obtained from six rats is reported as average percent of injected dose, plus or minus standard deviation.)

TABLE 4

Distrtibution Of I-125 In Rat Tissue Following Injection Of I-125
Labeled L(E)-Iodoallyl-β-methyl-3-trifluorophenyethylamine

|  | 5 Minutes | 30 Minutes | 60 Minutes |
| --- | --- | --- | --- |
| Blood | 0.37 ± 0.03 | 0.38 ± 0.02 | 0.33 ± 0.03 |
| Heart | 0.72 ± 0.10 | 0.29 ± 0.02 | 0.26 ± 0.03 |
| Lung | 1.50 ± 0.26 | 0.61 ± 0.05 | 0.54 ± 0.08 |
| Liver | 1.35 ± 0.13 | 0.53 ± 0.05 | 0.43 ± 0.06 |
| Spleen | 0.53 ± 0.05 | 0.29 ± 0.03 | 0.29 ± 0.05 |
| Kidney | 0.95 ± 0.09 | 0.54 ± 0.04 | 0.52 ± 0.06 |
| Adrenal | 1.58 ± 0.27 | 1.04 ± 0.16 | 1.47 ± 0.29 |
| Stomach | 0.41 ± 0.02 | 1.32 ± 0.24 | 1.03 ± 0.13 |
| Muscle | 0.44 ± 0.07 | 0.20 ± 0.02 | 0.06 ± 0.00 |

(Distribution data obtained from six rats is reported as average percent of injected dose, plus or minus standard deviation.)

The organ distribution with other labelled compounds such as [$^{11}$C]-N-methyl-L-β-methyl-3-trifluorophenyethylamine shows that the compound concentrated mainly in lung, liver, muscle and kidneys at 5 minutes. A slight initial heart uptake was observed at 5 minutes; however, the heart-to-lung ratio was very low. The lung activity washed out from 6.09% injected dose per organ at 5 minutes to 1.1% injected dose per organ at 60 minutes, while blood activity decreased only by 30% from 3.38% to 2.28% at 60 minutes. The kidney activity was high at first and then washed out with time. Muscle activity accounted for 31% of the dose per organ at 5 minutes and decreased to 13% at 60 minutes.

The enantiomer, $^{11}$C labeled N-methyl-D-β-methyl-3-trifluorophenyethylamine, showed similar organ distribution for heart, lung and liver activity. Lung activity was 6.32% injected dose per organ at 5 minutes and decreased to 1.3% at 60 minutes while liver activity seemed lower at 5 minutes than at 30 minutes. At 60 minutes, the liver activity was twice that of [$^{11}$C]-N-methyl-L-β-methyl-3-trifluorophenyethylamine. It is surprising that blood activity (dose per organ) increased with time as compared to [$^{11}$C]-N-methy-L-norfenfluramine. At 5 minutes, lung activity was 2.38% and increased to 9.5% at 60 minutes compared to that of [$^{11}$C]-N-methyl-L-β-methyl-3-trifluorophenyethylamine which decreased by 30%.

With D-N-methyl-β-methyl-3-trifluorophenylethylamine, the activities were less than about 1% injected dose per gram in most sections of the brain (hypothalamus, cerebellum, pons, cortex, striatum). In this case, there was almost no washout of activity from the different sections. At 30 minutes, the activity increased in most brain regions as compared to the decrease in all the regions with L-3-trifluorophenyethylamine.

In general, both tracers, L- and D-N-methyl-β-methyl-3-trifluorophenylethylamine were extracted by the brain with the L isomer in higher concentration. The D-tracer uptake increased slowly or stayed constant in the different levels for a period of 60 minutes while the L-isomer washed out from these regions.

This different biodistribution may explain the difference in the behavior of L-N-methyl-≠-methyl-3-trifluorophenylethylamine and D-N methyl-β-methyl-3-trifluorophenylethylamine.

Imaging studies in monkeys with the C-11 labeled enantiomers showed concentrations of activity in the brain. The frontal cortex, caudate putamen, and midbrain showed highest concentration. The activity washout with the L-enantiomer was faster than its D epimer. Preloading with fluoxetine (Prozac®) (3 mg/kg) showed lower uptake and faster brain washout, indicating that these analogs compete with fluoxetine for the same serotonin sites. A rat imaged with carbon-11 D-3-trifluorophenyethylamine revealed activity in the frontal cortex, caudate and putamen areas of the brain.

Weight changes for low dose (0.1 mg/kg) (Table 5) and high dose (0.3 mg/kg in multiple administration) (Table 6), were studied in rats. As evidenced in Table 5, a low dose injection once every three days resulted in weight gain according to the following order 4>2>1>3. In contrast, as shown in Table 6, a high dose twice in three days caused weight reduction as follows: 4>2>3>1. The N-propargyl derivative (compound 4) showed the highest weight change for the high and low dose as postulated from the lower catabolism and electronic effects.

TABLE 6

The Effect Of Multiple Dose Treatment With Two New N-substituted Phenylethylamines On Weight As Compared To Fenfluramine And Control

|  | *1 | *2 | *3 | *4 |
|---|---|---|---|---|
| Weight before 0.3 mg/kg Treatment 2 × /day | 411.2 ± 19.8 | 414.8 ± 52.5 | 402.8 ± 29.9 | 423.9 ± 13.97 |
| Weight after 3 days | 402.9 ± 20.3 | 392.5 ± 58.0 | 387.0 ± 15.0 | 387.0 ± 8.0 |
| Net Decrease | 8.3 g | 22.4 g | 15.8 g | 36.90 g |

(Data obtained from three rats is reported, plus or minus standard deviation.)

TABLE 6-continued

The Effect Of Multiple Dose Treatment With Two New N-substituted Phenylethylamines On Weight As Compared To Fenfluramine And Control

|  | *1 | *2 | *3 | *4 |
|---|---|---|---|---|

*1 = control
*2 = fenfluramine
*3 = D-N-methyl-methyl-3-trifluorophenylethylamine
*4 = N-propargyl-3-trifluorophenylethylamine
NOTE: values are reported ± standard deviation.

TABLE 5

The Effect Of A Low Dose (0.1 mg/kg) Treatment With Two New N-Substituted Arylalkylamines On Weight As Compared to And Control

|  | *1 | *2 | *3 | *4 |
|---|---|---|---|---|
| Weight Before Treatment | 385.0 ± 19.43 | 388.3 ± 37.3 | 381.0 ± 20.3 | 385.6 ± 14.0 |
| 0.1 mg/kg treatment Weight After 3 Days | 394.8 ± 23.1 | 393.5 ± 40.7 | 387.9 ± 18.50 | 395.4 ± 15.3 |
| 0.1 mg/kg treatment Weight After 6 Days | 411.2 ± 19.8 | 414.8 ± 52.5 | 402.8 ± 29.9 | 423.9 ± 13.97 |
| Net Increase | 25.3 g | 26.50 g | 21.80 g | 38.30 g |

Studies are from three rats for each point.
*1 = control
*2 = fenfluramine
*3 = D-N-methyl-methyl-3-trifluorophenylethylamine
*4 = N-propargyl-3-trifluorophenylethylamine
NOTE: values are reported ± standard deviation.

Equivalents

Those skilled in the art will recognize, or be able to ascertain using no more than routine experimentation, many equivalents of the specific embodiments of the invention described herein. Such equivalents are intended to be encompassed by the following claims.

We claim:

1. A compound having the structural formula:

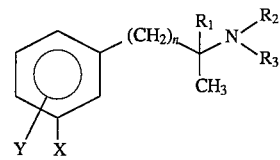

wherein,

X=CF$_3$, CH$_3$, C$_2$H$_5$ or Cl$_3$;

Y=Cl or Br ; ortho, para or meta to X;

n=1,2 or 3;

R$_1$=H and R$_2$ and R$_3$ =acyl, alkenyl and alkynyl groups; or

R$_1$=CH$_3$ and R$_2$ and R$_3$=H, alkyl, acyl, alkenyl and alkynyl groups.

2. A compound of claim 1 selected from the group consisting of N-propargyl-β-methyl-3-trifluorophenylethylamine, N-iodovinyl-β-methyl-3-trifluorophenylethylamine, and N,N-dimethyl-β-methyl-3-trifluorophenylethylamine.

3. A pharmaceutical composition comprising a meta substituted arylalkylamine compound of claim 1 and a pharmaceutically acceptable carrier.

4. A method for increasing the concentration of serotonin in a serotonergic gap junction in a subject comprising administering to the subject an effective amount of a compound of claim 3.

5. A method for treating depression in a subject comprising administering to the subject an effective amount of the composition of claim 3.

6. A method for treating obesity in a subject comprising administering to the subject an effective amount of a composition of claim 3.

7. A pharmaceutical composition comprising an effective amount of the compound of claim 1 and an effective amount of a thermogenic drug and an effective amount of a pharmaceutically acceptable carrier.

8. A method for treating in a subject comprising administering to the subject an effective amount of the composition of claim 7.

9. A method for quantitating the binding of serotonin or a serotonin ligand in a subject comprising administering to the subject a compostion of claim 1 and monitoring the subject by an appropriate means.

\* \* \* \* \*